(12) United States Patent
Metz et al.

(10) Patent No.: US 7,141,060 B1
(45) Date of Patent: *Nov. 28, 2006

(54) INSTRUMENT FOR INSERTING A PROSTHESIS TUBE CONNECTION

(75) Inventors: Ludwig Metz, deceased, late of Bestensee (DE); by Emma Helga Metz, legal representative, Bestensee (DE); by Katharina Metz, legal representative, Puschkinstrasse 14, DE-15741 Bestensee (DE); by Dietrich Metz, legal representative, Bestensee (DE); Andreas Gussmann, Kleinmachnow (DE)

(73) Assignee: Katharina Metz, Bestensee (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/181,833

(22) PCT Filed: Mar. 23, 2000

(86) PCT No.: PCT/EP00/02611

§ 371 (c)(1),
(2), (4) Date: May 2, 2003

(87) PCT Pub. No.: WO01/52769

PCT Pub. Date: Jul. 26, 2001

(30) Foreign Application Priority Data

Jan. 20, 2000 (DE) ................................ 100 02 318

(51) Int. Cl.
*A61F 2/06* (2006.01)

(52) U.S. Cl. ..................................... 623/1.11; 606/194

(58) Field of Classification Search ..................... None
See application file for complete search history.

(56) References Cited

U.S. PATENT DOCUMENTS 5,304,220 A * 4/1994 Maginot ..................... 128/898

(Continued)

FOREIGN PATENT DOCUMENTS

WO  WO 97/43961  11/1997

(Continued)

*Primary Examiner*—Anhtuan T. Nguyen
*Assistant Examiner*—Tuan V. Nguyen
(74) *Attorney, Agent, or Firm*—Fulbright & Jaworski L.L.P.

(57) ABSTRACT

The invention relates to an instrument for inserting a prosthesis tube connection between two blood vessels, especially arteries (12) or arterial areas, comprising a flexible, blood-impermeable connecting tube (11) which supports an expandable tubular metal screen (13) at at least one end, preferably only at one end, said screen being positioned at an angle to the longitudinal axis of the connecting tube and having a blood-tight inner lining and/or outer covering (15). Said screen extends in two opposite directions (11) from the end of the tube concerned, in a transversal T-bar. An expansion balloon (24) which can be expanded with a pressurised fluid is located inside the metal grid (13) and can be subjected to the action of the pressurised fluid through a pressurised fluid delivery tube (35) that is preferably guided through the connecting tube (11), for the purpose of expanding the metal screen (13). The invention is characterised in that the metal screen (13), together with the inner lining and/or the covering (15) and the expansion balloon (24) are held in a pivoted position in relation to the connection tube (11) at the proximal end of a catheter (28), in such a way that the transversal T-bar formed by the metal screen (13), the inner lining and/or the covering (15) and the expansion balloon (24) extends at least approximately in the longitudinal direction of the catheter (28).

22 Claims, 6 Drawing Sheets

U.S. PATENT DOCUMENTS

Figure 1:
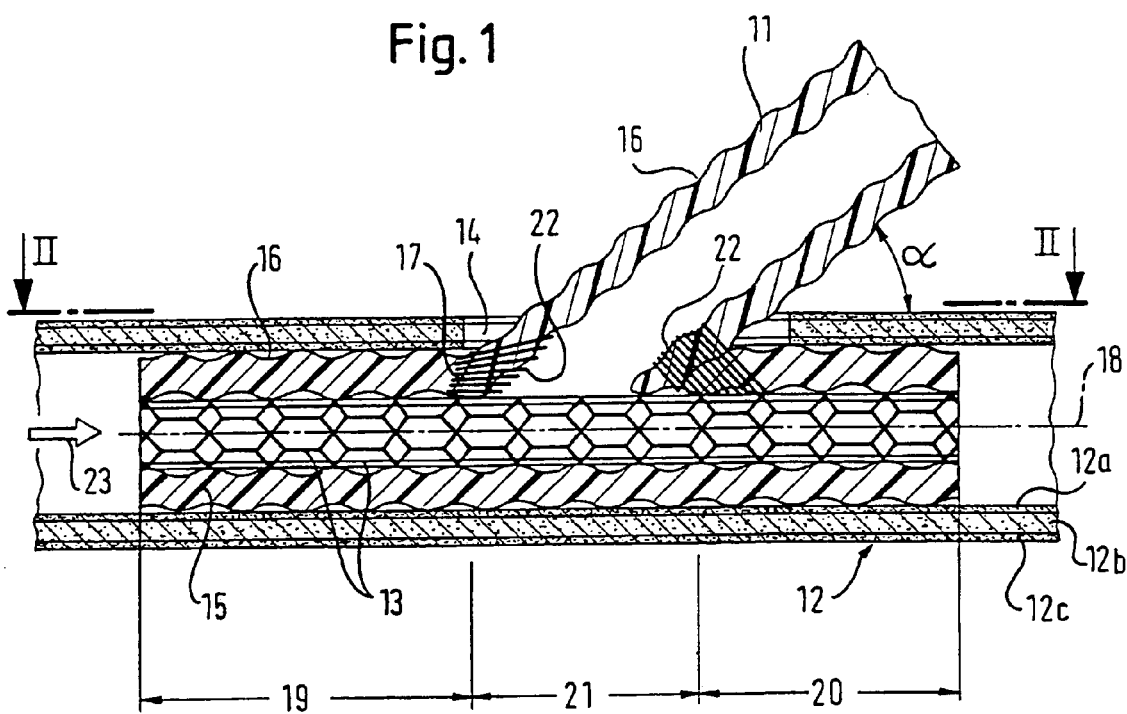

| | | | | |
|---|---|---|---|---|
| 5,443,497 A | * | 8/1995 | Venbrux | 623/1.13 |
| 5,755,778 A | * | 5/1998 | Kleshinski | 623/1.13 |
| 5,972,017 A | * | 10/1999 | Berg et al. | 606/198 |
| 5,984,955 A | * | 11/1999 | Wisselink | 623/1.35 |
| 6,019,788 A | * | 2/2000 | Butters et al. | 623/1.35 |
| 6,210,430 B1 | * | 4/2001 | Solem | 623/1.11 |
| 6,241,741 B1 | * | 6/2001 | Duhaylongsod et al. | 606/153 |

FOREIGN PATENT DOCUMENTS

| | | |
|---|---|---|
| WO | WO 98/19607 | 5/1998 |
| WO | WO 98/19629 | 5/1998 |
| WO | WO 00/16719 | 3/2000 |

* cited by examiner

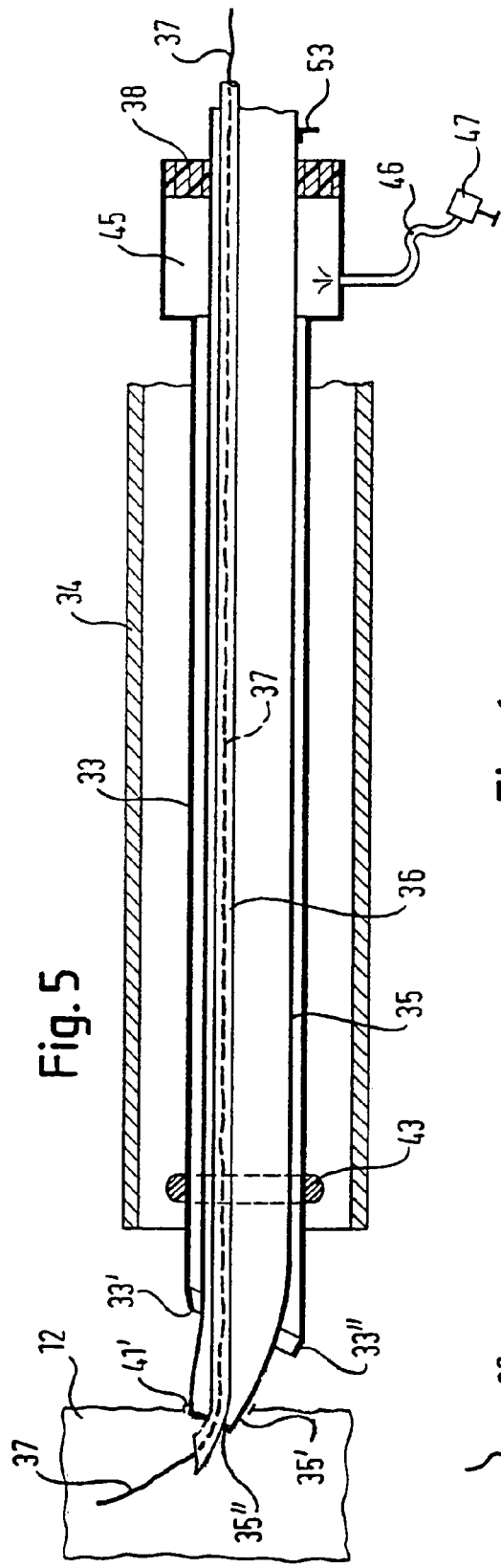
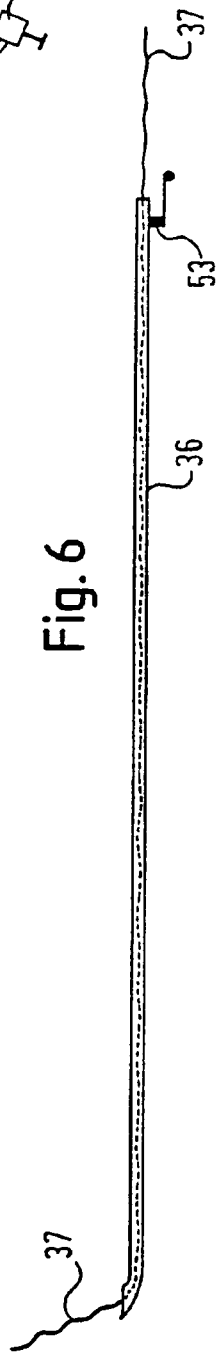
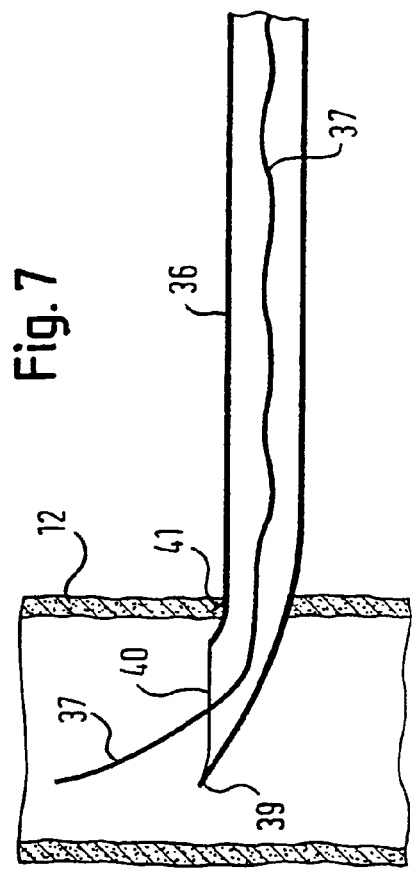
Fig. 5
Fig. 6
Fig. 7

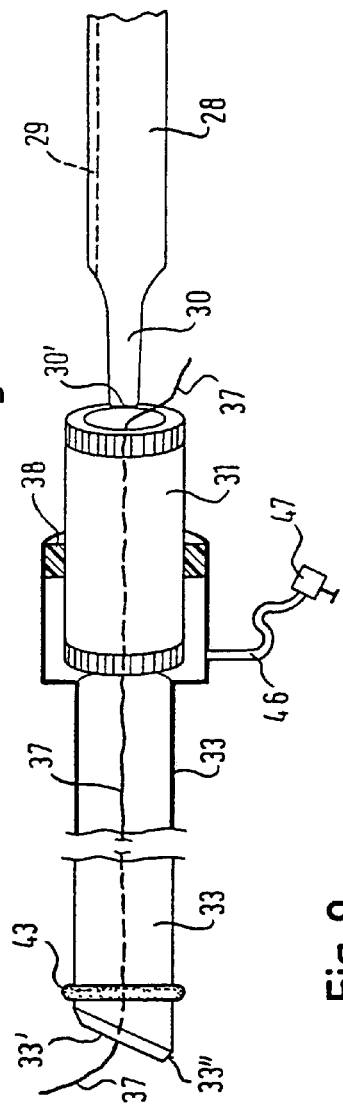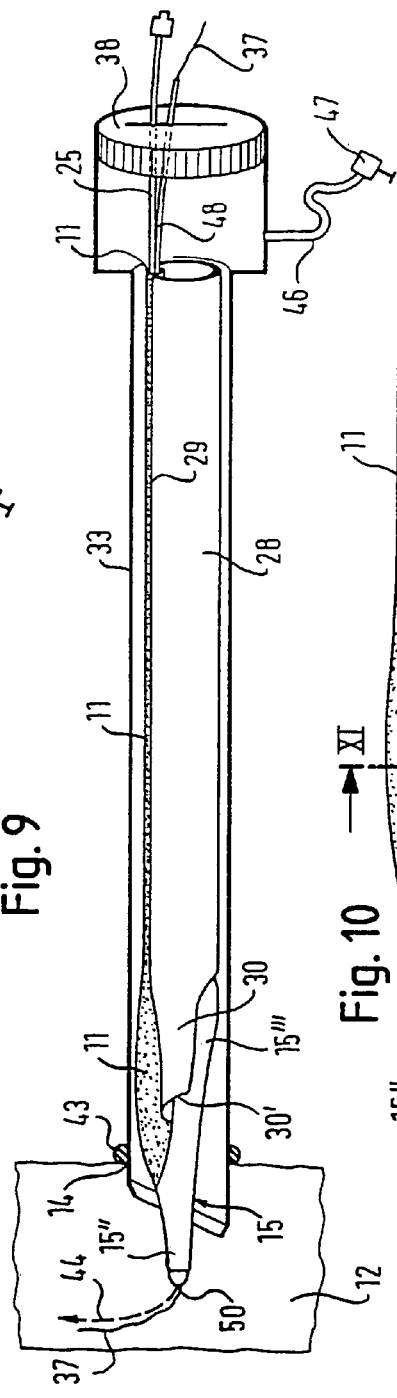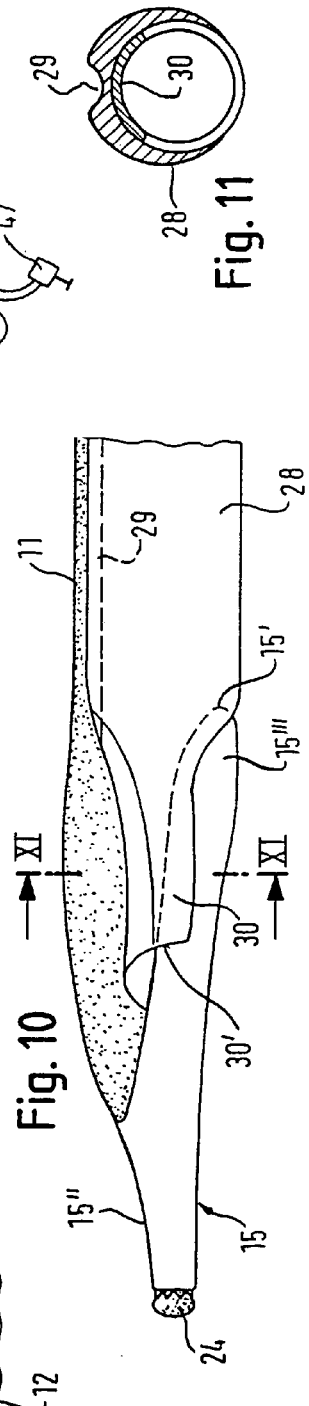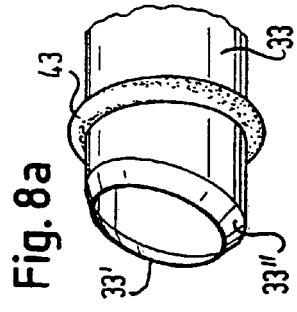

INSTRUMENT FOR INSERTING A PROSTHESIS TUBE CONNECTION

The invention relates to an instrument for inserting a prosthesis hose connection in accordance with the preamble of claim 1.

Such a prosthesis hose connection is known from the PCT application PCT/EP99/04192.

The present invention has as its aim an instrument for inserting the known prosthesis hose connection with which the metal grid (stent) of the known prosthesis hose connection can be introduced into and artery and expanded simply, reliably and with without the risk of injury such that subsequently a perfect seating of the metal grid in the artery is ensured without the requirement of suturing.

The features of the characterizing part of claim 1 are provided to satisfy this object.

The idea of the invention can therefore be seen in that, by pivoting the cross bar of a T formed by the metal grid with the inner lining and/or the covering toward the connecting hose and by holding it in this position by means of a catheter formed in this respect, first an overall elongate structure is provided which can preferably be inserted into an artery through a lock tube and an opening previously manufactured by puncturing and dilation, where the angle between the connecting hose and the metal grid is enlarged again by disabling a previously provided anchoring and the metal grid is brought into position. Subsequently, an expansion of the balloon disposed in the metal grid then takes place via the pressurized fluid delivery hose until the metal grid tightly contacts the inner wall of the artery, optionally with its covering, and is thus connected to this in a blood impermeable manner. In this connection, a repeated dilation is carried out to secure the dilation opening in the outlet region of the prosthesis. The connecting hose can then be connected at its other end in a blood conducting manner to the other artery, or to the other arterial region, which—if the relevant arterial region allows easy access—can take place by suturing or likewise by a metal grid with an inner lining and/or a covering.

In accordance with the invention, the catheter is expediently formed in accordance with claim 2.

The further developments in accordance with claims 3 and 4 are particularly advantageous because the release of the catheter from the connecting hose is hereby facilitated without the insertion of the metal grid into the artery being impeded.

The embodiment in accordance with claim 5 is of particular importance because the cross bar of a T can hereby be held in the longitudinal direction of the catheter tube until the insertion into the artery has taken place.

Advantageous further developments of this embodiment can be seen from claims 6 to 12. The combination of a channel-like projection and a distally connecting catheter hose makes possible a secure hold of the cross-bar of a T-like metal grid with an inner lining and/or a covering at least substantially parallel to the catheter axis or to the connecting hose led along its outer side up to the insertion into the artery.

Further advantageous embodiments of the invention, which describe advantageous components belonging to the insertion instrument, are characterized by claims 13 to 24.

Figure 2:
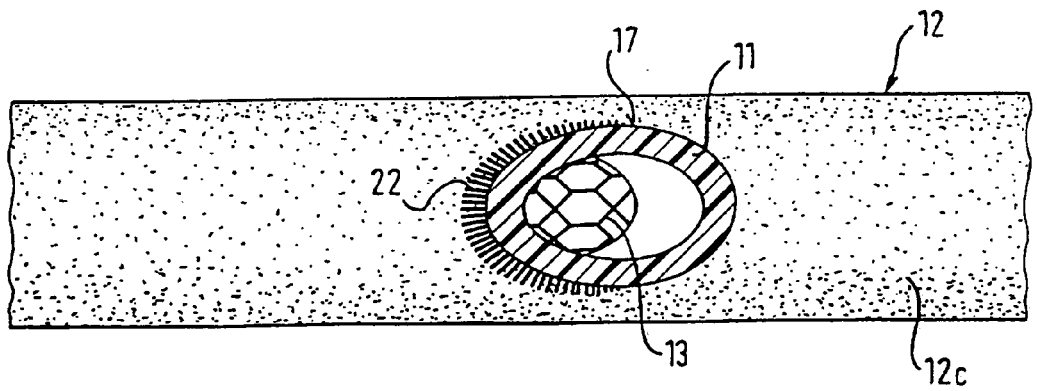
Figure 3:
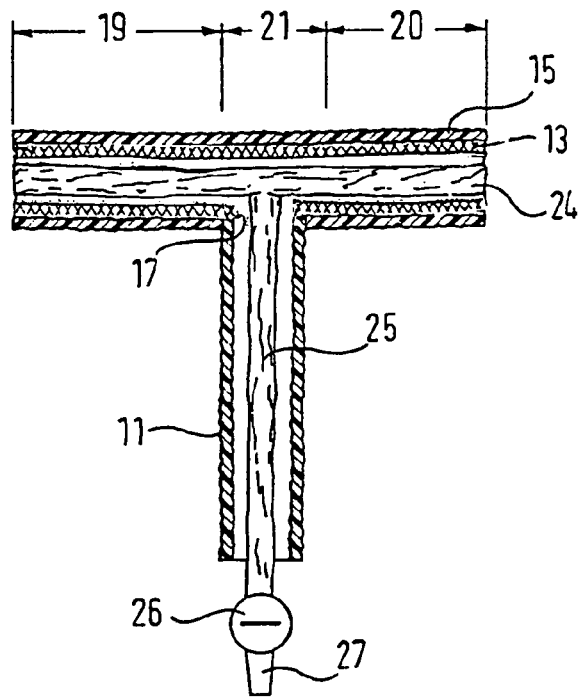
Figure 4:
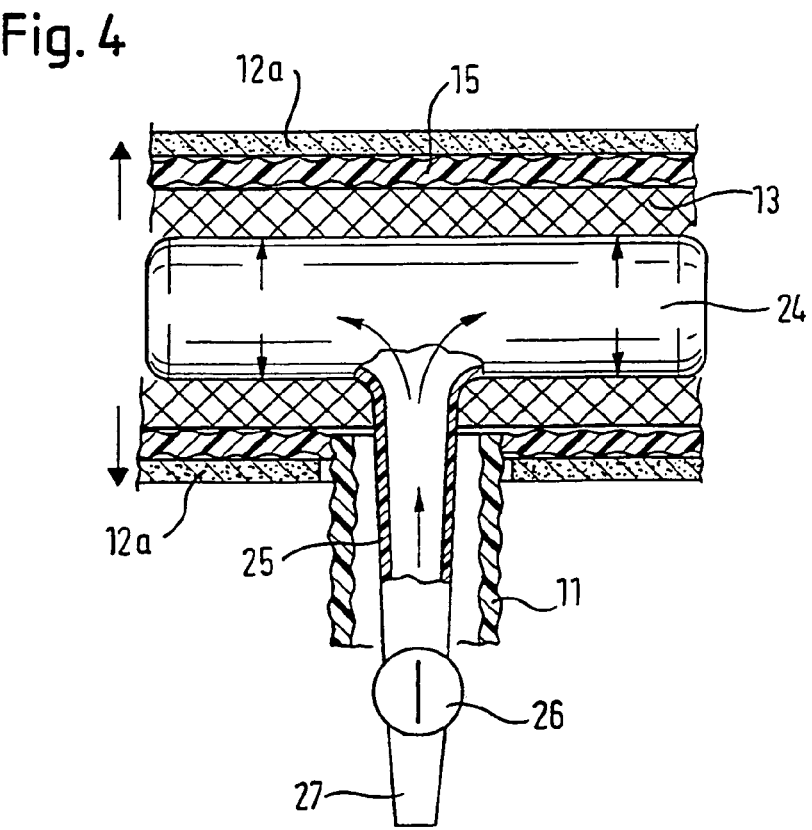
Figure 13:
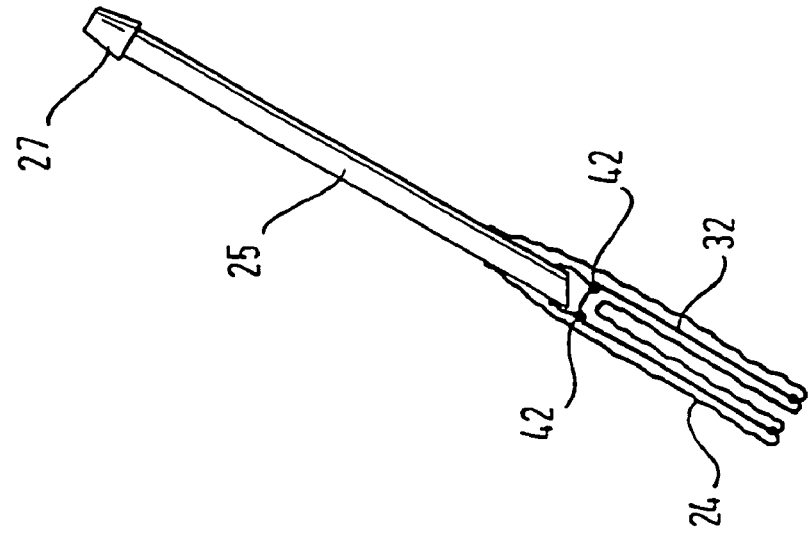
Figure 12:
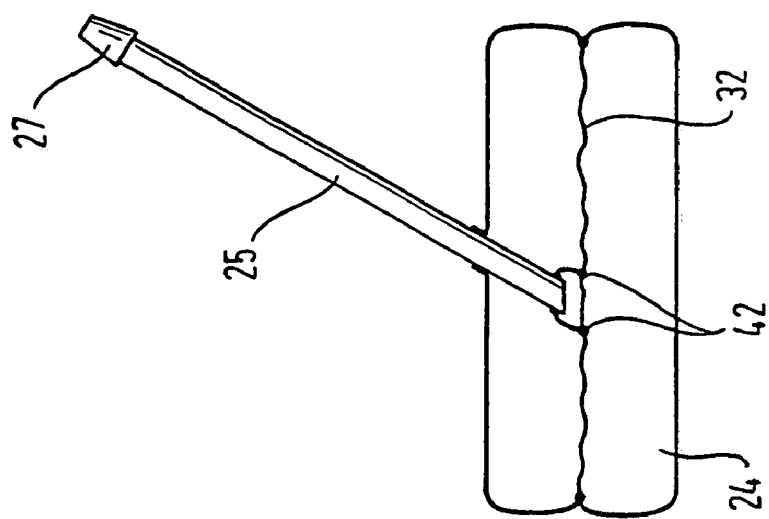
Figure 14:
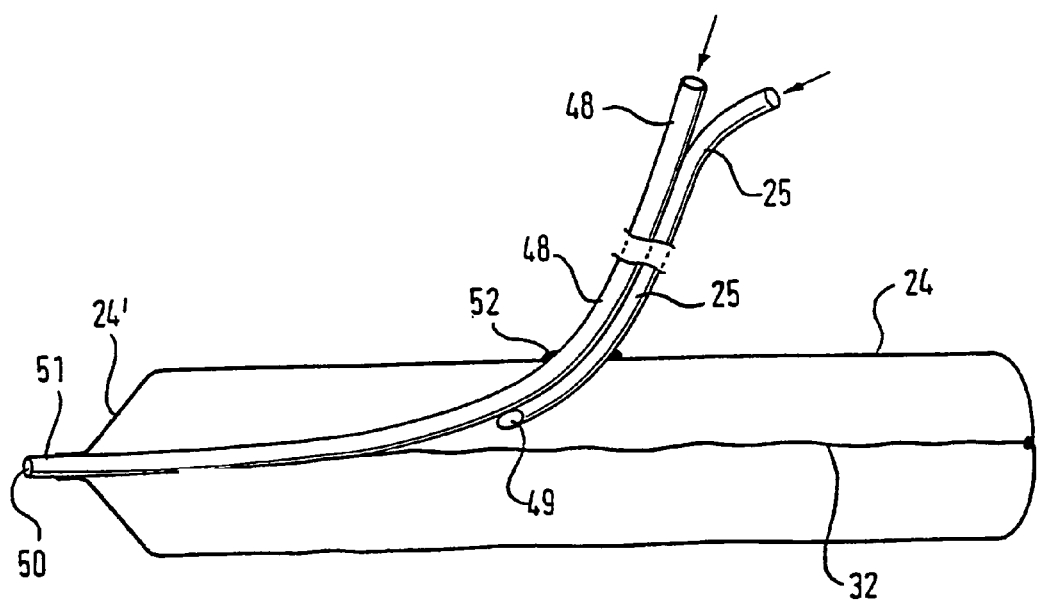

The invention will be described in the following by way of example with reference to the drawing, in which are shown FIG. 1 in a schematic longitudinal sectional view, the one end region of a prosthesis hose connection in accordance with the older application PCT/EP99/04192 after the introduction into an artery and expansion;

FIG. 2 a partly sectioned plan view of the object of FIG. 1 in accordance with the line II—II in FIG. 1;

FIG. 3 a schematic side view of a prosthesis hose connection in accordance with the invention in the folded together state with the introduced balloon and pressurized gas delivery hose before the inflation and expansion of the metal grid, with the artery receiving them not being shown;

FIG. 4 a somewhat enlarged view analog to FIG. 3 after the introduction of the covered metal grid into an artery and after the inflation of the balloon and the expansion of the metal grid;

FIG. 5 a schematically, partly sectioned side view of a trocar with a lock tube arranged therein, in which a dilation tube with a cannula is disposed which is shown arranged in an artery;

FIG. 6 a separate side view of the cannula arranged inside the dilation tube in accordance with FIG. 5 with a wire disposed therein and projecting from both ends;

FIG. 7 an enlarged sectional view of the proximal end region of only the cannula in accordance with FIGS. 5, 6 after puncturing an artery;

FIG. 8 a schematic side view of the lock tube in accordance with FIG. 5 in a shortened representation, with an insertion sleeve having been introduced into a valve at the distal end of the lock tube to enable a catheter tube shown behind it to be introduced into the lock tube without problem;

FIG. 8a an enlarged perspective view of the proximal end region of the lock tube in accordance with FIGS. 5 and 8;

FIG. 9 a schematic side view of the lock tube also shown in FIGS. 5 and 8 in the state introduced into an artery with a catheter arranged therein carrying a prosthesis hose connection;

FIG. 10 an enlarged section of the proximal end region of the catheter carrying the prosthesis hose connection in accordance with FIG. 9;

FIG. 11 a schematic sectional view in accordance with the line XI—XI in FIG. 10;

FIG. 12 a schematic side view of a preferred embodiment of a balloon in accordance with the invention with a delivery hose branching off it in the inflated state of the balloon;

FIG. 13 a schematic side view of the delivery hose and of the balloon in the deflated state during the pulling out of the connecting hose of the prosthesis hose connection (which is not shown) in accordance with the invention; and FIG. 14 an enlarged schematic side view of an expansion balloon preferably used in accordance with the invention with a pressurized gas delivery hose connector and guide passages for the wire shown in FIGS. 5 and 7.

In accordance with FIG. 1, a tube-shaped metal grid 13 is provided with a plastic covering 15. Such covered metal grids 13 (covered stents) are known from aorta surgery, for example, to dilate the major artery or to reduce dilated arteries or aorta sections in diameter or to seal burst aorta sections.

The covering 15 is provided at a point on its periphery remote from both ends with an elongate opening 17 in the direction of the central axis 18 of the metal grid 13, with the one end of a prosthesis connecting hose 11 being inserted into said elongate opening 17 at an angle α which, in accordance with FIGS. 3, 4 can also be 90°, and indeed such that the material of the hose 11 comes to rest on the metal grid 13. In this state, the end of the hose 11 is connected in a blood impermeable manner to the regions of the covering 15 surrounding the opening 17 by a suture 22. In this manner, a connection region 21 for the connecting hose 11 is formed at the metal grid 13 provided with the covering 15 and the metal grid 13 with the covering 15 extends from this in both opposite longitudinal directions. The part 19 extending against the direction of the blood flow 23 is in this connection somewhat longer than the part 20 of the metal grid 13 with the covering 15 extending in the direction of the blood flow 23.

As can be seen from FIG. 2, the opening 17 is oval due to the oblique connection of the end region of the connecting hose 11 having a circular cross-section to the covering 15, with the longer axis of the opening 17 extending in the direction of the central axis 18 of the metal grid 13.

In FIGS. 1 and 2, the described hose connection is shown arranged in an artery 12 which consists of three layers, and indeed of the inner intima 12a, the middle media 12b and the outer adventitia 12c. The metal grid 13 with the covering 15 is introduced into the artery 12 in that a round or oval opening 14 is provided in this corresponding to the opening 17. Subsequently, first the longer part 19 is inserted in the form folded in accordance with FIG. 3 through the opening 14 into the artery 12 by means of an insertion instrument described further below with reference to FIGS. 5 to 11, and indeed so far that the shorter part 20 also reaches into the inside of the artery 12 when folded and can subsequently be displaced into the position shown in FIG. 1.

In accordance with FIG. 3, an elongate balloon 24 extending in the direction of its longitudinal axis is introduced in deflated form into the folded metal grid 13, with a delivery tube 25 branching off to the side of this in the central region which is guided through the connecting tube 11 and opens into a valve 26 which can be opened or closed by hand and which has a connection cone 27 which can be connected to a pressure source. A pressurized gas, but also a pressurized liquid such as an X-ray contrast medium solution, can be delivered through the delivery hose 25.

In contrast to the embodiment in accordance with FIG. 1, the connecting tube 11 branches off perpendicularly from the metal grid 13 with the covering 15 in the embodiment in accordance with FIGS. 3 and 4.

After the cross bar of a T of the prosthesis tube connection formed by the metal grid 13 with the covering 15 in accordance with FIG. 3 has been introduced with the deflated balloon 24 into an artery 12 in the manner described further below, the connection cone 27 is connected to a pressurized air source and the valve 26 is opened, whereupon, in accordance with FIG. 4, pressurized air can flow into the inside of the balloon 24 such that the balloon 24 inflates and an expansion of the metal grid 13 with the covering 15 takes place for so long until a fixed seating of the metal grid 13 with the covering 15 is ensured within the artery 12 without suturing being required.

The angle α is selected in accordance with FIG. 1 such that the blood flowing in the direction of the arrow 23 cannot flow from the inside of the metal grid 13 into the hose 11 at an angle of 90°, but rather at a much smaller angle than 90°, for example 45°. Some of the blood can, however, flow through the metal grid 13 past the hose 11 into the part of the artery 12 disposed behind the metal grid 13. In accordance with FIGS. 3, 4, however, a perpendicular branching off of the connecting hose 11 is also possible.

At the other end of the prosthesis hose 11 not shown in the drawing, a metal grid 13 with a covering 15 can likewise be arranged in a manner similar to that in FIG. 1 in order to also be able to connect the other end of the hose 11 in a similar manner to another artery or to another arterial region without the making of a suture being necessary for the connection.

The connecting hose 11 can, however, also be sutured to the artery at the relevant end provided that the connection region is easily accessible from the outside.

Generally, instead of the covering 15, or additionally to this, an inner lining, which is not shown in the drawing, can also be provided at the metal grid 13. In this case, the inner lining would have to be provided with a suitable closed opening in the region of the fastening region 21. The metal grid 13 will preferably also have a throughgoing opening in the region of the opening 17.

Both the covering 15 and the hose 16 are provided with a peripheral corrugation 16, whereby the required flexibility of the hose 11 and of the combination of metal grid 13 and covering 15 is increased.

The opening 17 should be 0.8 to 1.8 cm long in the direction of the central axis 18.

The insertion of the prosthesis hose connection in accordance with the invention fixed on a balloon catheter in the folded state into the artery or aorta can take place via an insertion instrument having a lock of a maximum inner diameter of 12 mm, as will be described in the following with reference to FIGS. 5 to 11.

In accordance with FIG. 5, the lock tube 33 is pushed forward into the region of the artery 12 into which the described prosthesis hose connection should be introduced by a trocar 34 inserted into the body of a patient.

A dilation tube 35 is arranged inside the lock tube 33 and has a slightly smaller diameter and in which a cannula 36 is freely movably disposed which is shown separately in FIG. 6 and receives a relatively stiff guide wire 37 which extends from the front to the rear end and whose end region defined for the reception in the artery 12 is flexible and which projects substantially from both ends in accordance with FIG. 6.

The dilation tube 35 which tapers conically at least in the proximal region, is hollow at the interior and receives the puncture cannula 36 consists at its tip of soft, supple plastic and expands from the tip to the rear over a length from 10 cm to 15 cm. It projects forwardly out of the lock tube 33. It is thus ensured that when the opening is made in the aorta 12, it can only dilate slowly and thus larger lacerations are avoided from which bleeding could occur.

In accordance with the invention, the cannula 36 is shaped in its proximal end region in accordance with the representation of FIG. 7, i.e. it there has a relatively sharp tip 39 and is curved such that its discharge opening 40 is located at a side of the cannula 36. The flexible end of the wire 37, which is to be inserted into the artery and which is inserted from the distal end of the cannula 36, also exits there. In this manner, the diversion of the wire 37 inserted through the cannula 36 in the direction of the axis of the artery 12 is promoted.

With the lock tube 33 disposed in the position of FIG. 5 close to the artery 12, the cannula 36 is first moved out of the proximal opening 35" of the dilation tube by a suitable manipulation and inserted into the wall of the artery 12 such that a starting opening 41 is punctured there (FIG. 7).

The dilation tube 35 which surrounds the cannula 36 in accordance with FIG. 5 and whose tip 35' tapers toward the artery 12 is then inserted into the starting opening 41, whereby in accordance with FIG. 5 an expanded opening 41' is provided in the desired manner and size. At the same time, the cannula 36 is retracted with the end of the wire 37 remaining in the artery 12. Then the lock tube 33 itself, in accordance with FIG. 9, is inserted into the prepared opening 41' of the artery 12, whereby the final opening 14 is provided in the artery 12.

The proximal end 33' of the lock tube 33 is, in accordance with FIGS. 5 and 8, 8a, somewhat inclined with respect to the longitudinal axis of the lock tube 33 and has an insertion inclination 33" all around, behind which a sealing flange 43 is located which extends all around and sealingly contacts the artery 12 when the lock tube is inserted into the artery 12 (FIG. 9).

Once the lock tube 33 is disposed in the opening 14 of the artery 12, the cannula 36 and the dilation tube 35 are pulled out of the lock tube 33 which has a valve 38 at its distal end and which is made by flexible material provided with passage slits such that the different components described can be inserted into the lock tube 33 in a manner largely impermeable to pressure and blood.

An insertion sleeve 32 in accordance with FIG. 8 is now inserted from the rear through the valve 38 of the lock tube 33 to provide an axial passage for the insertion of a catheter 28 in accordance with the invention whose formation will be described in detail with reference to FIGS. 9, 10, 11.

The catheter 28 is formed over the larger part of its length as a circularly cylindrical tube in whose outer periphery an axial groove 29 is disposed, while a channel-like, lip-shaped projection 30 is formed at the front end which is partly circularly cylindrical and merges continuously into the actual catheter tube 28. The projection 30 has a somewhat smaller radius than the catheter tube 28 and is concentric to the catheter tube 28.

While the catheter tube 28 is shown in FIGS. 8 and 11 without a prosthesis hose connection arranged thereon, FIGS. 9 and 10 reproduce the catheter tube 28 with a prosthesis hose connection arranged thereon in accordance with the invention.

In accordance with FIGS. 9 and 10, the connecting hose 11 of the prosthesis hose connection in accordance with the invention is laid along the radial outer side of the projection 30 in the axial groove 29 at the outer periphery of the catheter tube 28. The pressurized gas delivery hose 25, which leads to the balloon 24, is disposed inside the connecting tube 11 and projects, in accordance with FIG. 9, backwardly and outwardly out of the connecting hose 11 through the valve 38 in order to there be connected in a manner not shown to a pressurized gas source.

The cross bar of a T formed by the metal grid 13 with the covering 15 at the proximal end of the connecting hose 11 is bent in the manner visible from FIGS. 9 and 10 relative to the connecting hose 11 such that it extends at least substantially in the direction of the axis of the catheter tube 28 and almost parallel to the connecting hose 11.

So that the cross bar of a T remains in this position largely resiliently adjoining the connecting hose 11, the distal end 15' of the rear part 15''' of the cross bar of a T is slightly inserted into the catheter tube 28, as is indicated by a broken line in FIG. 10. The gusset between the part 15''' and the connecting hose 11 is disposed at the end face 30' of the projection 30. The balloon 24 should project somewhat beyond the metal grid 13 at both ends in order to reduce the risk of injury on insertion and to promote the releasing effect described in the following. The front part 15" of the cross bar of a T projects forwardly beyond the end face 30' of the projection 30, as can in particular be seen from FIG. 10.

FIG. 14 shows that the pressurized gas delivery hose 25 is inserted into the interior of the balloon 24 via an adhesive point 52 and has a gas outlet opening 49 there. A hose-shaped guide passage 48 extends parallel to the delivery hose 25, likewise enters into the interior of the balloon 24 in the region of the adhesive point 52, which is disposed in the fastening region 21 (FIG. 1), and is there bent in the direction of the axis of the balloon 24. The guide passage 48 exits the balloon 24 in the form of a passage end piece 51 at the insertion end face 24' and there forms a wire insertion opening 50. The guide passage 48 is defined for the reception of the wire 37 (FIGS. 5, 7).

The two tubes 25, 48 which extend parallel and closely to one another up to a connection piece (not shown) can also be arranged concentrically to one another such that the guide passage 48 is arranged centrally and the delivery hose 24 is arranged concentrically around it. The delivery hose 25 and the guide passage 48 are expediently made as a double lumen catheter. In this manner, the delivery hose 25 and the guide passage 48 form a uniform structure.

For reasons of a clear representation, the balloon 24 is shown in the inflated state in FIG. 14.

Before the catheter 28 is inserted through the valve 38 into the lock hose 33, the wire 37 projecting out of the insertion sleeve 31 at the rear in accordance with FIG. 8 is inserted into the wire insertion opening 50 (FIG. 14). On the insertion of the catheter 28 through the insertion sleeve 31 into the lock tube 33, the wire 37 is displaced inside the guide passage 48.

When the catheter 28 with the prosthesis hose connection arranged thus is inserted through the insertion sleeve 31 (FIG. 8) into the lock tube 33, the prosthesis hose connection remains in this elongate state for so long until the proximal part 15'' of the cross bar of a T in accordance with FIG. 9 has entered into the artery 12. Here, the front part 15" (FIG. 9) of the cross bar of a T is guided by the wire 37 which is inserted into the wire insertion opening 50 (FIG. 14) and which extends up to and into the artery 12. The wire 37 here extends approximately as is indicated in FIG. 9. Some pressure is now put into the folded balloon 24 via the delivery hose 25, said balloon 24 being disposed inside the metal grid 13 from the start in accordance with FIG. 3 and being connected to a pressure source (not shown) via the delivery hose 25 laid through the connecting hose 11.

It is achieved by a slight inflation of the balloon 24 that the distal end 15' of the cross bar of a T (FIG. 10), at which the balloon 24 also protrudes somewhat, projects out of the catheter tube 28, whereupon the cross bar of a T again attempts, as a result of the elasticity of the connection between the connecting hose 11 and the covering 15, to adopt its normal angular position relative to the connecting hose 11. The return of the cross bar of a T into its normal position relative to the connecting tube 11 can be supported in that the catheter is pulled back somewhat on insertion into the artery. If the catheter 28 in accordance with FIG. 9 is now further inserted into the artery, then the cross bar of a T moves—guided by the wire 37 extending sufficiently far into the artery 12—in the direction of the broken line 44, i.e. in the direction of the axis of the artery 12, with both the still folded metal grid 13 with the covering 15 and the flexible projection 30 being able to adopt a shape curved corresponding to the broken line. The end region of the balloon 24 projecting out of the proximal end due to the slight inflation reduces the risk of injury.

As soon as the distal end 15' of the cross bar of a T (FIG. 10) has reached up to and into the artery 12, the cross bar of a T of the prosthesis hose connection is disposed in a position extending parallel to the artery 12. By a subsequent retraction of the connecting hose 11, the cross bar of a T ultimately achieves its final position such as is reproduced, for example, in FIGS. 1 and 4.

The catheter tube 28 can now be removed and the pressure in the balloon is increased via the delivery hose 25 to, for example 10 atm whereupon the balloon 24 radially dilates the metal grid 13 and presses the covering 15 tightly onto the inner wall of the artery 12.

After the prosthesis hose connection has been fixed in the artery 12 in this manner, the balloon 24 is deflated via the delivery hose 25 and the delivery hose 25 can be pulled out through the connecting hose 11 with the deflated balloon 24, with it adopting the shape in accordance with FIG. 13.

After the lock tube 33 has also been removed, the prosthesis hose connection is fixed and ready for use in the desired manner impermeable to blood in the artery 12.

In accordance with FIG. 12, a core 32 can be arranged inside the balloon 24 for stabilization which extends along its axis and up to which the pressure tube 25 extends to be secured to the core there at 42. The core 32 can also be provided in the embodiment in accordance with FIG. 14 and be partly formed by the axial region of the guide passage 48. In this manner, in particular the pulling out of the deflated balloon 24 in accordance with FIG. 13 is promoted and too great a bulging of the balloon 24 at its end faces avoided.

The implant system is therefore inserted into the abdominal cavity via a lying trocar 34 (FIG. 34). It is usual in endoscopic operations to insert a working trocar 34 into the abdominal wall of the patient. The working trocar 34 is equipped with a valve such that a plurality of instruments can be introduced alternately without the pneumoperitoneum which has been produced collapsing.

The lock tube 33, with the dilation tube 35 containing the cannula 36 and the inlying wire 37, is inserted so far by the trocar 34 in the manner indicated in FIG. 5 such that the dilation tube 35 comes to rest with its flexible tip 35' on the desired point of the aorta 12. Then, in accordance with FIG. 7, the cannula 36 is inserted into the artery 12 to form the starting opening 41. Subsequently, in accordance with FIG. 5, the tip 35' of the dilation tube 35 is inserted into the artery 12 to form the somewhat larger opening 41'.

A hemostatic valve 38 is disposed in a dilated end region 45 at the end of the lock tube 33. It consists of silicone which is notched a plurality of times in a crossed manner to allow an outward sealing, on the one hand, and the insertion of instruments, on the other hand. Thus, no blood can escape when the components disposed at the interior of the lock tube 33 are replaced.

After, in accordance with FIG. 7, a puncture of the aorta 12 has been produced by the cannula 36 and subsequently the opening 14 of a desired size has been produced by the dilation tube 35 and the lock tube 33 (FIG. 9), the dilation tube 35, with the cannula 36 disposed therein, is removed with, however, the guide wire 37 remaining in the aorta 12.

After removal of the dilation unit 35, 36, the lock tube 33 is flushed with a heparin/NaCl solution, for which purpose a hose connector 46 with a three-way valve 47 is provided at the distal end of the lock tube 33 (FIGS. 5, 8, 9).

As a result of the special design of the cannula 36 in accordance with FIG. 7, it is ensured that the wire 37 can be inserted into the artery 12 in the cranial direction. After the wire 37 has been inserted, it can serve as the guide for the dilation hose 35 which dilates the punctured starting opening 41 in the artery 12 at least approximately to the desired dimension 41' (FIG. 5).

The wire 37 is inserted so far into the aorta 12 that it does not slide out of the artery 12 on the retraction of the cannula 36.

The insertion of the dilation tube 35 into the punctured opening 41 of the artery 12 is therefore necessary so that no bleeding occurs. The cannula 36 has a larger diameter than the guide wire 37 so that, when the cannula 36 is removed from the starting opening 41, a bleeding could occur if the tip 35' of the dilation tube 35 has not previously been inserted into the starting opening 41.

The sealing flange 43 in the proximal end region of the lock tube 33 preferably consists of silicone. Only when the sealing flange 43 contacts the wall of the artery 12, i.e. the distal end 33' of the lock tube 33 has penetrated into the artery 12 to provide the opening 14 in the artery 12, is the dilation tube 35 removed.

When the dilation tube 35 has been pulled out of the lock tube 33, the lock fills with blood. The system is then flushed with an NaCl solution and heparin 5000 IE-100 ml via the three-way valve and the hose connector 46. The valve 38 at the end of the lock tube 33 is impermeable here. No penetration of air or bleeding can occur.

The insertion sleeve 31 (FIG. 8) serves for the pushing through of the catheter 28 containing the prosthesis hose connection (stent graft system). Since the hemostatic valve 38 is relatively taut, if the prosthesis were introduced directly an injury to the same could result. To prevent this, the valve 38 is held open by the insertion sleeve 31 to thus allow the catheter 28 to be introduced into the lock tube 33 without danger together with the prosthesis hose connection. To avoid any bleeding, the front part of the catheter 28 should be inserted into the insertion sleeve 31 already before the introduction into the lock tube 33. The diameter of the catheter 28 should correspond to the inner diameter of the insertion sleeve 31 to avoid the passing through of blood to the rear.

The catheter 28 is then pushed over the guide wire 37 (FIG. 8) still lying in the lock tube 33 by inserting the distal end of the wire 37 into the wire insertion opening 50 (FIGS. 9, 14) until the front end of the catheter 28 in accordance with FIG. 9 has entered into the artery 12 and the cross bar of a T 15 is positioned in the artery 12. The wire 37 satisfies the task, in addition to the location and positioning of the cross bar of a T 15, of securing the total system, i.e. it serves as the guide line for all parts to be introduced. Only subsequently is the guide wire 37 pulled out and finally the balloon 24 slightly inflated via the delivery hose 25 so that the cross bar of a T 15", 15''' of the prosthesis hose connection becomes free, as has been described above. After the cross bar of a T of the prosthesis hose connection has been arranged freely and completely in the artery 12, the cross bar of a T can be brought into the correct position in the artery 12 by pulling back the insertion instrument. The lock tube 33 is still located in the position within the artery 12 visible from FIG. 9 here.

A diversion or substantial change of the trocar 34, which is only shown in FIG. 5, is not necessary. After the balloon 24 has been fully inflated, that is the cross bar of a T of the prosthesis hose connection in accordance with the invention is disposed in the correct position in the artery 12, the lock tube 33 is pushed out of the artery 12 by the pressure produced in the artery 12 by means of the balloon 24. In this connection, work is carried out at pressures around 10 atm. If the lock tube 33 should here only stick a few mm in the wall of the artery 12, it can remain in this position. If the balloon 24 is then pulled into the connecting hose 11 in the deflated state, it can be again inflated somewhat by feeding in pressurized gas, whereby the lock tube 33 is automatically pushed around 1 to 2 cm away from the artery 12.

The lying guide wire 37, which is introduced into the artery 12 via the puncturing cannula 36, serves for the definition of the direction and the positional control of the dilation tube 35, of the lock tube 33 and of the catheter 28.

The wire 37 is preferably stiff and has a flexible tip of 50 mm to 100 mm in length which is defined for the insertion into the artery.

The projection 30 at the proximal end of the catheter 28 should be curved and dimensioned such that it covers the covering 15 of the metal grid 13 by more than half. Since the material of the projection 30 is soft and yielding, the cross bar of a T 15", 15''' can be released from its anchoring in the catheter hose 28 with a filling of less than 10 ml.

The insertion sleeve 31 also remains in the lock tube 33 for the bleeding control. Only when the balloon 24 has been completely inflated and is kept under pressure can the insertion sleeve 31 be removed. To avoid bleeding, the insertion sleeve 31 in turn has to be arranged tightly inside the valve 38 opened by it.

Markings 53 (FIGS. 5, 6) are expediently provided in the end regions of the different components (e.g. 36, 35) to be inserted into the lock tube 33, said markings 53 cooperating with counter-markings at the lock tube 33 to be able to recognize in the manipulations when the proximal end of the relevant component has reached its working position. This is particularly important with the cannula 36 (FIGS. 6, 7) so that the correct degree of penetration of the cannula 36 into the artery 12 can be found without problem.

The approximate dimensions of the individual components of the insertion instrument in accordance with the invention are as follows:

Inner diameter of the catheter 28: 8 to 15 mm.

Depth of the axial groove 29: 2 to 3 mm.

Length of the projection 30: 10 to 30 mm.

Length of the insertion sleeve 31: 60 mm.

Diameter of the insertion sleeve 31: 9 to 16 mm.

Diameter of the wire 37: 0.1 mm.

Diameter of the dilation tube 35: 8 to 15 mm.

Length of the conical tip 35' of the dilation tube 35: up to 100 mm.

Spacing of the end 33' of the lock tube 33 from the sealing flange 43: 0.4 mm to 0.6 mm.

Inner diameter of the lock tube 33: 9 to 18 mm.

Diameter of the balloon 24: 8 mm to 22 mm.

Length of the balloon 24: 40 mm.

Expansion pressure of the balloon 24: 8 atm to 15 atm.

Diameter of the delivery hose 25: 3 mm.

Length of the delivery hose (and of the guide passage 48): 60 cm.

REFERENCE NUMERAL LIST 11 prosthesis connecting hose
12 artery
13 metal grid
13' part of the metal grid
13" part of the metal grid
13''' free end of the metal grid
14 longitudinal section
15 covering
15' distal end
15" part
15''' part
16 peripheral corrugation
17 opening
18 central axis
19 upstream part
20 downstream part
21 fastening region
22 suture
23 direction of blood flow
24 balloon
24' end face
25 delivery hose
26 valve
27 connection cone
28 catheter
29 axial groove
30 projection
30' end face
31 insertion sleeve
32 core
33 lock tube
33' end
33" insertion incline
34 trocar
35 dilation tube
35' tip
35" opening
36 cannula
37 wire
38 valve
39 tip
40 discharge opening
41 starting opening
42 fastening point
43 sealing flange
44 line
45 end region
46 tube connection
47 three-way valve
48 guide channel
49 gas outlet opening
50 wire insertion opening
51 channel end piece
52 adhesion point
53 marking

The invention claimed is:

1. An instrument for inserting a prosthesis hose connection between two blood vessels, in particular arteries (12), or arterial regions, comprising a flexible connecting hose (11) which is impermeable to blood and which carries an expandable tubular metal grid (13) arranged at an angle to its longitudinal axis at at least one end, and preferably only at one end, said metal grid (13) having a blood impermeable inner liner and/or covering (15) and extending from the relevant end of the hose (11) like a cross bar of a T in two opposite directions, with an expansion balloon (24) expandable by a pressurized fluid being disposed within the metal grid (13) and being preferably charged with pressurized fluid via a pressurized fluid delivery hose (25) guided through the connecting hose (11) for the expansion of the metal grid (13), characterized in that the metal grid (13) with the inner liner and/or covering (15) and the expansion balloon (24), is held at the proximal end of a catheter (28) in a state pivoted relative to the connecting hose (11) such that the cross bar of a T formed by the metal grid (13), with the inner liner and/or covering (15) and the expansion balloon (24), thereby extends at least approximately in the longitudinal direction of the catheter (28); and the connecting tube (11), with the delivery tube (25) arranged therein, is arranged at the outer side of the catheter (28) in the longitudinal direction of the same.

2. An insertion instrument in accordance with claim 1, characterized in that the catheter (28) is made as a rod or hose.

3. A prosthesis tube connection and an insertion instrument in accordance with claim 1, characterized in that an axial groove (29) accepting the connecting tube (11) is provided in the outer wall of the catheter (28).

4. An instrument for inserting a prosthesis hose connection between two blood vessels, in particular arteries (12), or arterial regions, comprising a flexible connecting hose (11) which is impermeable to blood and which carries an expandable tubular metal grid (13) arranged at an angle to its longitudinal axis at at least one end, and preferably only at one end, said metal grid (13) having a blood impermeable inner liner and/or covering (15) and extending from the relevant end of the hose (11) like a cross bar of a T in two opposite directions, with an expansion balloon (24) expandable by a pressurized fluid being disposed within the metal grid (13) and being Preferably charged with pressurized fluid via a pressurized fluid delivery hose (25) guided through the connecting hose (11) for the expansion of the metal grid (13), characterized in that the metal grid (13) with the inner liner and/or covering (15) and the expansion balloon (24), is held at the proximal end of a catheter (28) in a state pivoted relative to the connecting hose (11) such that the cross bar of a T formed by the metal grid (13), with the inner liner and/or covering (15) and the expansion balloon (24), thereby extends at least approximately in the longitudinal direction of the catheter (28);

the proximal end region of the catheter (28) is open at one side and the part (15''') of the cross bar of a T pivoted toward the connecting tube (11) lies in this opening and is preferably releasably held with its distal end (15') at the catheter (28) in the position extending at least substantially parallel to the catheter axis, while the other part (15'') of the cross bar of a T pivoted away from the connecting tube (11) projects forwardly beyond the proximal end of the catheter (28); and the side opening of the proximal end region of the catheter (28) is realized by provision of a flexible, lip-shaped projection (30) at the proximal end of the catheter (28), along which the part (15''') of the cross bar of a T pivoted toward it extends at least in part.

5. A prosthesis tube connection and an insertion instrument in accordance with claim 4, characterized in that the connecting tube (11) and the part (15''') of the cross bar of a T pivoted toward it extend on opposite sides of the projection (30) along the same.

6. A prosthesis tube connection and an insertion instrument in accordance with claim 4, characterized in that the projection (30) is made in channel-like form and the hose shape of the catheter (38) continues at least substantially in part, with the channel-like projection (30) preferably being arranged at least substantially concentrically to the catheter hose (28).

7. A prosthesis tube connection and an insertion instrument in accordance with claim 4, characterized in that the radius of the projection (30) is slightly smaller than that of the catheter hose (28).

8. A prosthesis tube connection and an insertion instrument in accordance with claim 4, characterized in that the projection is slightly shorter than the part (15''') of the cross bar of a T received in it such that the free end (15') of this part (15''') reaches somewhat into the catheter hose (18) and the cross bar of a T is thus held at least approximately parallel to the catheter hose (28).

9. A prosthesis tube connection and an insertion instrument in accordance with claim 8, characterized in that the overlapping of the part (13'') of the metal grid (13) received by the projection (18) with the catheter hose (28) is only so large that the part (13'') can snap out of the catheter hose (28) by some pressure generation in the delivery tube (25) or balloon (24).

10. A prosthesis tube connection and an insertion instrument in accordance with claim 4, characterized in that the periphery of the flexible projection (30) is so restricted and the flexibility is so large that, on insertion into an artery (12), it can bend out of the insertion direction into the direction of the artery.

11. An instrument for inserting a prosthesis hose connection between two blood vessels, in particular arteries (12), or arterial regions, comprising a flexible connecting hose (11) which is impermeable to blood and which carries an expandable tubular metal grid (13) arranged at an angle to its longitudinal axis at at least one end, and preferably only at one end, said metal grid (13) having a blood impermeable inner liner and/or covering (15) and extending from the relevant end of the hose (11) like a cross bar of a T in two opposite directions, with an expansion balloon (24) expandable by a pressurized fluid being disposed within the metal grid (13) and being preferably charged with pressurized fluid via a pressurized fluid delivery hose (25) guided through the connecting hose (11) for the expansion of the metal grid (13), characterized in that the metal grid (13) with the inner liner and/or covering (15) and the expansion balloon (24), is held at the proximal end of a catheter (28) in a state pivoted relative to the connecting hose (11) such that the cross bar of a T formed by the metal grid (13), with the inner liner and/or covering (15) and the expansion balloon (24), thereby extends at least approximately in the longitudinal direction of the catheter (28); and a lock hose (33) is provided which is tightly insertable into an opening (32) of the artery (12) and whose inner diameter is so large that the catheter hose (28) can be axially guided through.

12. A prosthesis tube connection and an insertion instrument in accordance with claim 11, characterized in that the lock hose (33) is arranged inside a trocar (34) which is insertable into the body of the patient from the outside.

13. A prosthesis tube connection and an insertion instrument in accordance with claim 11, characterized in that the expansion balloon (24) has a core (32), preferably flexible, which stabilizes it in the longitudinal direction.

14. A prosthesis tube connection and an insertion instrument in accordance with claim 11, characterized in that, at least at the insertion end (24'), preferably, however, at both ends, the balloon (24) projects somewhat beyond the metal grid (13), with the inner liner and/or covering (15).

15. A prosthesis tube connection and an insertion instrument in accordance with claim 11, characterized in that a valve (38) is provided at the rear end of the lock hose (33) through which the different instruments (28, 31, 35, 36, 37) can be inserted in at least a largely pressure tight manner.

16. A prosthesis tube connection and an insertion instrument in accordance with claim 15, characterized in that an insertion sleeve (31) is provided for the catheter hose (28) and can be inserted in a blood impermeable manner through the valve into the rear end region of the lock hose (33).

17. A prosthesis tube connection and an insertion instrument in accordance with claim 11, characterized in that a dilation hose (35) is provided which is arranged in the lock hose (33) instead of the catheter (28) and tapers in the direction toward the artery (12) to be punctured in the proximal end region.

18. A prosthesis tube connection and an insertion instrument in accordance with claim 17, characterized in that at least the tip (35') of the dilation hose (35) is elastic and somewhat bent.

19. A prosthesis tube connection and an insertion instrument in accordance with claim 17, characterized in that a cannula (36), with which the artery (12) of a patient can be punctured, is arranged inside the dilation hose (35).

20. A prosthesis tube connection and an insertion instrument in accordance with claim 19, characterized in that the cannula opening (40) is arranged to the side behind the tip (39) and the cannula wall is concavely curved with respect to the cannula opening (40).

21. A prosthesis tube connection and an insertion instrument in accordance with claim 19, characterized in that a wire (37) stiff in shear is provided inside the cannula (36) and is, however, flexible and elastic at least in the end region to be inserted into the artery and, with the cannula (36) inserted into the artery (12) of the patient, can be inserted through the former into the artery (12).

22. A prosthesis tube connection and an insertion instrument in accordance with claim 21, characterized in that a throughgoing channel (48) is provided for the reception of the wire (37) at or in the expansion balloon (24) and delivery tube (25).

* * * * *